US010299886B2

(12) United States Patent
Tallon

(10) Patent No.: US 10,299,886 B2
(45) Date of Patent: May 28, 2019

(54) DENTAL APPARATUS AND METHOD

(71) Applicant: Tallon Dental Products LLC, Branson, MO (US)

(72) Inventor: Richard Dale Tallon, Branson, MO (US)

(73) Assignee: Tallon Dental Products LLC, Branson, MO (US)

( * ) Notice: Subject to any disclaimer, the term of this patent is extended or adjusted under 35 U.S.C. 154(b) by 5 days.

(21) Appl. No.: 15/030,846

(22) PCT Filed: Nov. 3, 2014

(86) PCT No.: PCT/US2014/063727
§ 371 (c)(1),
(2) Date: Apr. 20, 2016

(87) PCT Pub. No.: WO2015/066633
PCT Pub. Date: May 7, 2015

(65) Prior Publication Data
US 2016/0242869 A1    Aug. 25, 2016

Related U.S. Application Data

(60) Provisional application No. 61/898,623, filed on Nov. 1, 2013.

(51) Int. Cl.
| | |
|---|---|
| *A61C 3/14* | (2006.01) |
| *A61C 1/05* | (2006.01) |
| *A61C 1/06* | (2006.01) |
| *A61C 1/08* | (2006.01) |
| *A61C 1/18* | (2006.01) |

(52) U.S. Cl.
CPC ................ *A61C 3/14* (2013.01); *A61C 1/052* (2013.01); *A61C 1/06* (2013.01); *A61C 1/081* (2013.01); *A61C 1/186* (2013.01)

(58) Field of Classification Search
CPC .. A61C 3/14; A61C 1/052; A61C 1/06; A61C 1/081; A61C 1/186
USPC ................................ 433/141, 4, 5, 159, 160
See application file for complete search history.

(56) References Cited

U.S. PATENT DOCUMENTS

| | | | | |
|---|---|---|---|---|
| 1,327 A | * | 9/1839 | McConnell | A61C 3/14 433/158 |
| 165,808 A | * | 7/1875 | Durham | A61C 3/14 433/146 |

(Continued)

OTHER PUBLICATIONS

USPTO/ISA, PCT/US2014/063727, PCT Search Report and Written Opinion dated Feb. 13, 2015, Tallon Dental Products LLC (6 pgs).

*Primary Examiner* — Heidi M Eide
*Assistant Examiner* — Mirayda A Aponte
(74) *Attorney, Agent, or Firm* — Crawford Maunu PLLC

(57) ABSTRACT

Various aspects are directed to dental extraction and dental extraction devices. As may be implemented in accordance with one or more embodiments herein, a dental extraction apparatus includes an engagement component that extracts teeth from patients' mouths by engaging with and applying a torque to a tooth. An input torque component translates received input torque to the engagement component. A torque controller operates with the input torque component and the engagement component to limit the applied torque, relative to input torque provided via the input torque component.

17 Claims, 6 Drawing Sheets

(56) References Cited

U.S. PATENT DOCUMENTS

| | | | | |
|---|---|---|---|---|
| 2,503,499 | A | * | 4/1950 | Livermont ............ B25B 13/466 |
| | | | | 464/37 |
| 2,626,029 | A | | 1/1953 | Gutterman |
| 3,018,677 | A | * | 1/1962 | Mutolo ............... B25B 23/1427 |
| | | | | 81/483 |
| 3,195,704 | A | * | 7/1965 | Linsker ................ B25B 23/145 |
| | | | | 173/15 |
| 6,162,053 | A | * | 12/2000 | Hollander ............ A61C 8/0089 |
| | | | | 433/141 |
| 6,481,317 | B1 | * | 11/2002 | Reyes .................... B25B 13/12 |
| | | | | 81/129 |
| 2001/0005576 | A1 | | 6/2001 | Rogers et al. |
| 2004/0101805 | A1 | * | 5/2004 | Golden .................... A61C 3/14 |
| | | | | 433/159 |
| 2006/0014119 | A1 | | 1/2006 | Bouneff |
| 2007/0256527 | A1 | | 11/2007 | Phan |
| 2011/0159459 | A1 | * | 6/2011 | Darwish ................. A61C 3/14 |
| | | | | 433/118 |
| 2011/0256502 | A1 | * | 10/2011 | Katz ....................... A61C 3/14 |
| | | | | 433/114 |

* cited by examiner

DENTAL APPARATUS AND METHOD

BACKGROUND

Extracting teeth can be a challenging task to carry out with regard to patient comfort and operator skill. For example, the application of force to remove teeth may be difficult to control. Moreover, trained dentists or other technicians are often not available, such that the manner in which to extract teeth and the control of applied force by inexperienced individuals may exacerbate issues relating to proper removal of teeth and patient comfort.

SUMMARY

Various example embodiments are directed to a dental extraction apparatus and related methods, as may be implemented to address challenges such as those discussed above.

According to an example embodiment, a dental extraction apparatus includes an engagement component that engages with a tooth for extraction, and a torque controller that operates with the engagement component to limit force applied to the tooth. The torque controller and engagement component are operative to readily extract teeth, while providing a pre-set amount of force in which to do so.

In various embodiments, the torque controller is operative to provide respective torques that are tailored to two or more types of teeth to be extracted, with preset torque settings that relate to those teeth. By combining this aspect with the torque-limiting control, a predefined extraction technique is controlled and also facilitated. In this context, relatively unskilled individuals can extract teeth while addressing challenges, including those discussed above.

In accordance with another embodiment, a dental extraction apparatus includes an engagement component that extracts teeth from patients' mouths by engaging with and applying a torque to teeth. An input torque component translates received input torque to the engagement component. A torque controller operates with the input torque component and the engagement component to limit the torque applied to the teeth, relative to input torque provided via the input torque component.

The above discussion/overview is not intended to describe each embodiment or every implementation of the present disclosure. The figures and detailed description that follow also exemplify various embodiments.

DESCRIPTION OF THE FIGURES

Various example embodiments may be more completely understood in consideration of the following detailed description in connection with the accompanying drawings, in which.

Figure 1:
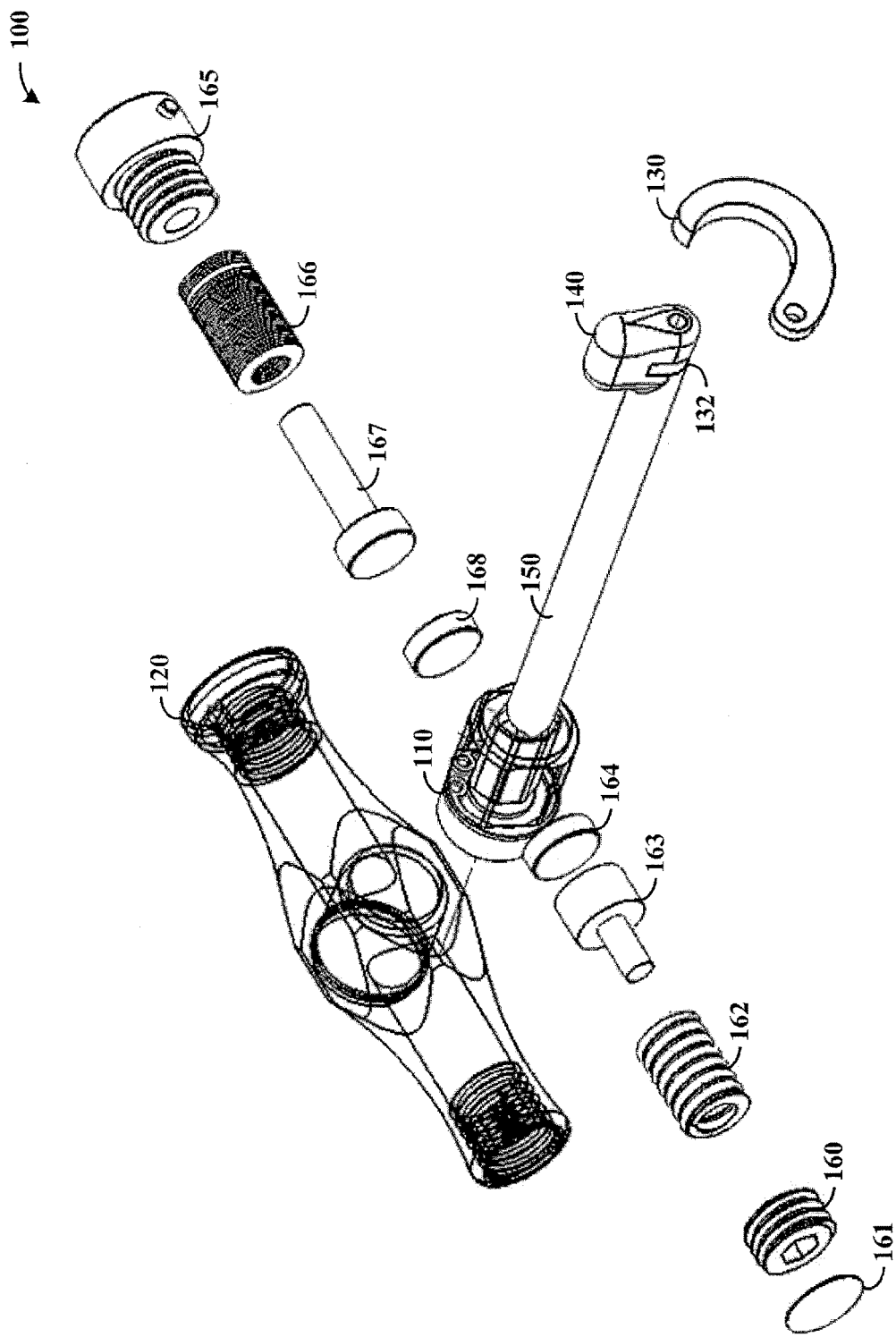
FIG. 1 shows a dental extraction device, in accordance with an example embodiment.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are believed to be applicable to a variety of different types of apparatuses, systems and methods involving dental extraction. While not necessarily so limited, various aspects may be appreciated through a discussion of examples using this context.

In accordance with another example embodiment, an apparatus and/or method involves a dental extraction apparatus. The dental extraction apparatus has an engagement component that extracts a tooth from a patient's mouth by engaging with and applying a torque to the tooth. A torque controller operates with the engagement component to limit the torque applied to the tooth. In connection with one or more embodiments, it has been discovered/recognized that, by providing a preset torque and related instruction relative to type of tooth, age, gender or other physiological condition, force-limited tooth extraction is facilitated. This force-limitation can be implemented with hand-applied torque as well as torque applied using one or more powered approaches, such as pneumatic power, hydraulic power or electrical power.

In some embodiments, the torque controller operates with the engagement component to limit the torque applied to a tooth based upon an adjustable torque setting corresponding to one of at least two predefined torques. In some implementations, the torque controller includes a slip clutch that limits the torque as such, based upon the adjustable torque setting. In certain implementations, the slip clutch mechanically slips in response to a torque input that is greater than a current torque-limit setting, and translates the torque input into a torque output that is applied to the tooth and that is limited in value to the current torque-limit setting. In other implementations, the slip clutch translates an input torque to an output torque that is applied to the tooth, and disengages the input torque from the output torque in response to the input torque exceeding a torque limit. Limiting of torque in this regard may be implemented in one or more of a variety of manners, such as in connection with the approaches shown in the Figures.

Various example embodiments are directed to a dental extraction apparatus having a slip-clutch torque controller that limits an amount of force applied during dental extractions. The torque controlled slip-clutch facilitates removal of teeth, in that respective levels of torque can be applied based upon a particular tooth that is to be removed. Such an approach may, for example, involve the use of a pre-set torque for respective types of teeth to be extracted, in which the device has two or more such predefined torque settings.

In various contexts, the torque applied can be controlled, and limited (e.g., as relative to the use of dental forceps), to elevate a tooth from the alveolar socket. Further, limiting torque in this manner, such as by implementing a torque limit setting based upon tooth type and/or location, can mitigate tooth fractures and the application of a force that may otherwise be too high.

In some implementations, the apparatus includes a force-absorbing component that protects tissue on an alveolar ridge on a buccal or facial side of a tooth being extracted. Such an absorbing component may include, for example, rubber or other flexible material.

Various materials are used to suit one or more applications. In some embodiments, at least a portion of the apparatus that engages with a patient includes a material, such as stainless steel, which is amenable to high-heat sterilization. Where a force-absorbing component is used, such a component may also include a material, such as a silicone, which is amenable to high-heat sterilization.

In certain embodiments, an extraction apparatus as described herein operates using two or more interchangeable engagement components that engage with a tooth. Such components may include, for example, "hooks" for lingual engagement of the tooth based on tooth type (e.g., molar, premolar or anterior teeth). In some embodiments, one such component exhibits a curvature for third molars.

In accordance with a particular embodiment, an engagement component is placed in contact with a tooth, and a force absorbing component (e.g., a silicone bumper) is placed on a buccal or facial aspect. A torque setting is applied to an adjustable torque-limiting component for the particular type of tooth being extracted, and/or in accordance with other aspects such as gender, age, and bone density shown on a radiograph.

Figure 4:
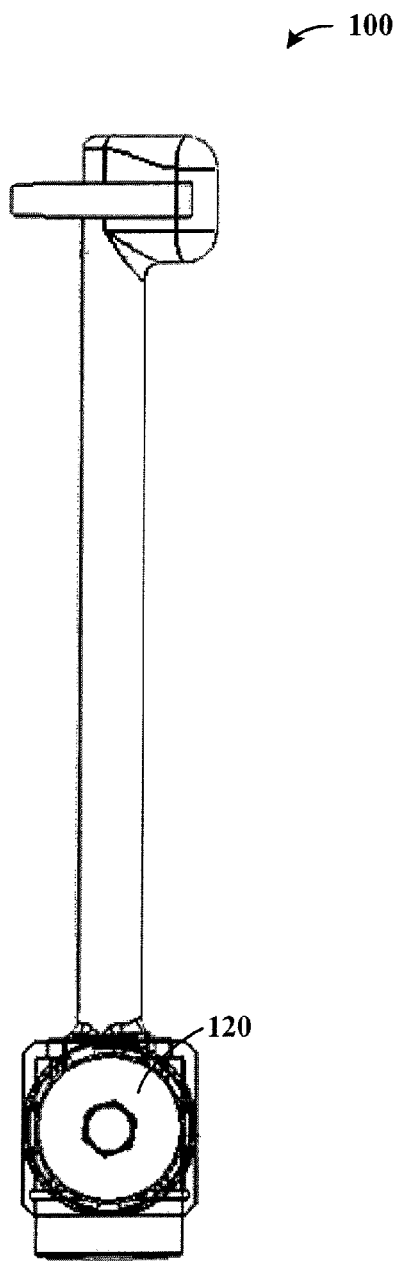
FIG. 4 shows another view of the dental extraction device, in accordance with another example embodiment.
Figure 5:
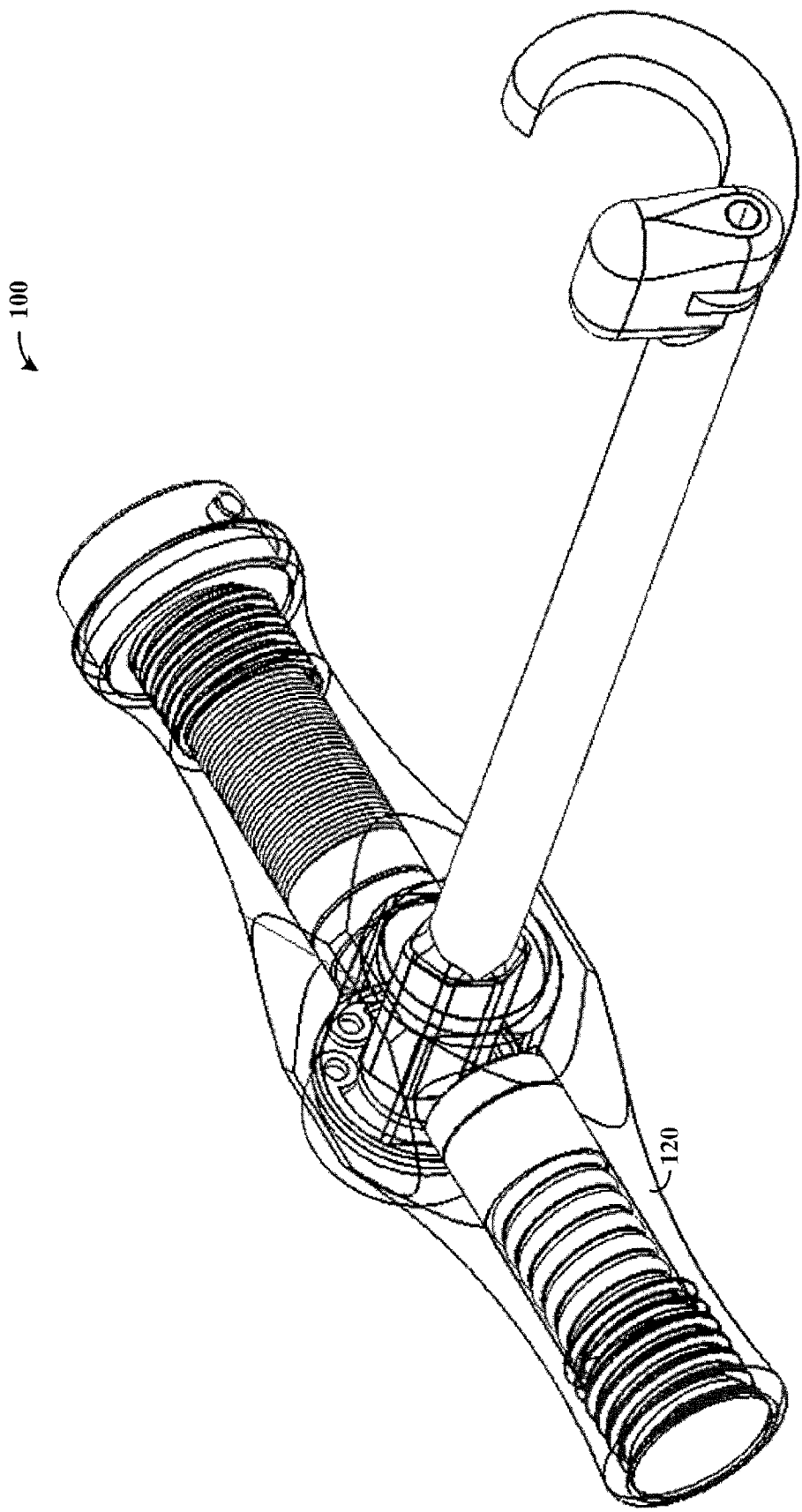
FIG. 5 shows another view of the dental extraction device, in accordance with another example embodiment.
Figure 6:
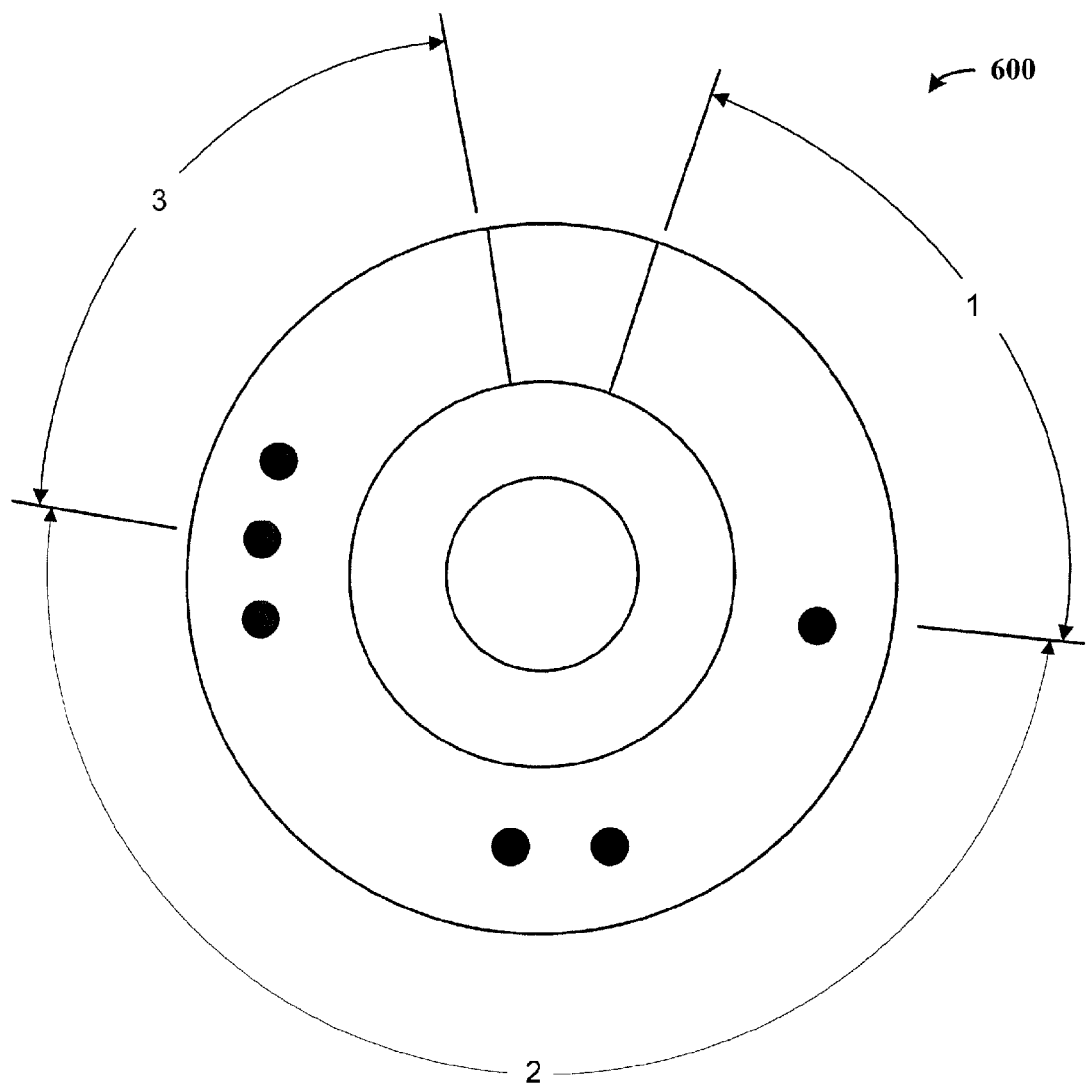
FIG. 6 shows a torque-limiting apparatus, in accordance with another example embodiment.

In addition, various embodiments may be implemented in connection with those shown in the underlying priority application, U.S. Provisional Patent Application No. 61/898,623 entitled "Dental Apparatus and Method," which is fully incorporated herein by reference. For instance, apparatus components such as those shown in FIGS. 1-4 of the provisional application may be implemented with the claimed apparatus and approach. The torque setting positions as shown in FIG. 5 of the provisional application may also be similarly implemented, with application to regions of a patient's mouth as shown in FIG. 6 of the provisional application. Further, torque may be limited with a spring-type apparatus as shown in FIGS. 7-14 of the provisional application. For instance, spring-like structures shown in a handle section facilitate the application of a limited torque, based upon torque limit settings. In some implementations, an apparatus as shown in FIGS. 7-14 of the provisional application is implemented in connection with the torque-limiting approaches shown in FIGS. 5 and 6 of the provisional application, to apply three fixed torque settings. In various embodiments, spring-type components, as well as threaded adjustable-type components, are implemented to effect the setting of predefined torques as discussed herein.

In accordance with a particular embodiment, a dental extraction apparatus includes an engagement component that extracts teeth from patients' mouths by engaging with and applying a torque to teeth. An input torque component translates received input torque to the engagement component (e.g., as generated via pneumatic power, hydraulic power and electrical power). A torque controller operates with the input torque component and the engagement component to limit the torque applied to the teeth, relative to input torque provided via the input torque component.

The torque controller operates in a variety of manners. For instance, a spring or other adjustable force component may be used to provide slip under certain torque conditions. In some embodiments, the torque controller operates with the input torque component and the engagement component to limit the torque applied to the tooth to a predefined torque, by limiting translation of the input torque to the engagement component based upon an adjustable torque setting provided by the torque controller and corresponding to one of at least two predefined torques. In another embodiment, the torque controller includes a slip clutch that limits the torque applied to the tooth, based upon the adjustable torque setting. The slip clutch may, for example, operate by mechanically slipping in response to a torque input that is greater than a current torque-limit setting, and translating the torque input into a torque output that is applied to the tooth and that is limited in value to a torque-limit setting at which the torque controller is set. In certain applications, the slip clutch translates the input torque to an output torque that is applied to the tooth via the engagement component, and disengages at least a portion of the input torque from the output torque in response to the input torque exceeding a torque limit.

In a particular embodiment, the torque controller limits the torque applied according to three preset torque limits. These limits include a first low torque setting via which the engagement component applies sufficient torque to extract anterior teeth, a second intermediate torque setting via which the engagement component applies sufficient torque to extract premolars, and a third high torque setting via which the engagement component applies sufficient torque to extract molars and canines. The engagement component is operable for applying a torque under the second intermediate torque setting that is higher than torque applied under the first low torque setting, and lower than torque applied under the third high torque setting.

The input torque component is implemented in a variety of manners. In some implementations, the input torque component includes a handle component operable for grasping by a human hand. The torque controller is located within the handle component and includes a spring that applies pressure against a torque-limiting plate that operates to slip in response to a torsion that provides a radial force against the spring that exceeds a force applied by the spring to the torque-limiting plate.

In some embodiments, the apparatus further includes a shaft connecting the input torque component at a proximal end of the shaft with the engagement component at a distal end of the shaft. The shaft translates torque from the input torque component to the engagement component, as limited by the torque controller. In some implementations, a force-absorbing component is adjacent a distal end of the shaft and cushion the patient's mouth by absorbing force applied via the shaft and providing a pivot point about which the torque is applied to the tooth. In certain implementations, the engagement component includes a coupling that couples to a variety of hook-type structures and to implement the torque to manipulate one of the hook-type structure coupled to the apparatus to extract a tooth. Such structures may be implemented for specific types of teeth or different types of patients, as discussed herein.

Turning now to the Figures, FIG. 1 shows a dental extraction apparatus 100, in accordance with another example embodiment. The apparatus 100 includes a torque-limiting component 110 near a handle region 120, and a hook-like engagement portion 130 that engages with a tooth, and is coupled via a slot region 132. In some implementations, a distal end of the apparatus 100 includes a force-absorbing/bumper portion at 140. A shaft 150 connects the handle region 120 with the engagement portion 130.

FIG. 1 also shows an exploded view of components that are implemented within the handle 120. Beginning on what is shown as the left side, the apparatus includes a first threaded end 160, shown by way of example with a hexagonal receiver and a cap 161. A spring 162 is coupled between the end 160 and support component 163, which has an elongated region that extends inside the spring and acts as a base upon which the spring is compressed, and a spacer/slip component 164 engages adjacent the shaft 150. On what is shown as the right side of the handle 120, a threaded end 165 is adapted for screwing into the handle 120, and shows a set screw by way of example for affixing the end (and which may also be implemented with end 160). A series of washers 166 are between the threaded end 165 and a support component 167, which also has an elongated region that extends inside the washers 166 and acts as a base upon which the washers can engage. A spacer/slip component 168 engages adjacent the shaft 150.

While shown with specific spring and washer-based torque control, the apparatus 100 may implement a variety of types of slip control. For instance, the washers 166 may be implemented with a spring component, and the spring 162 may be implemented with washer components, or a combination thereof. Further, additional types of spring components may be used to suit various applications.

Figure 2:
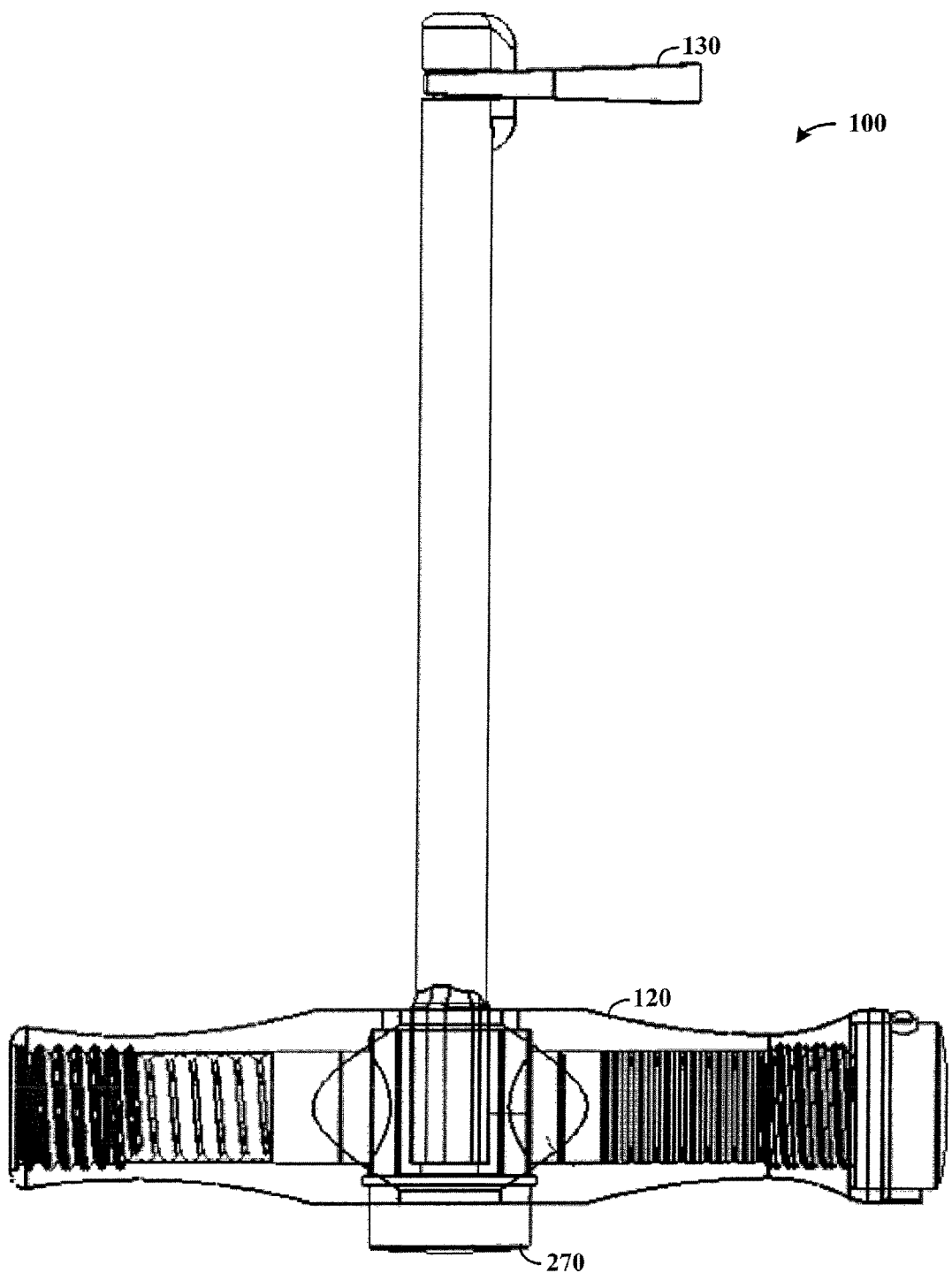
FIG. 2 shows another view of the dental extraction device, in accordance with another example embodiment.

FIGS. 2-5 show assembled views of the apparatus 100. FIG. 2 shows a side view with each end of the handle 120 extending in left and right directions as shown, the exploded components shown in FIG. 1 having been inserted within the handle, and the engagement portion 130 coupled in the slot 132 of FIG. 1. A variety of types of engagement portions 130 can be used, to suit different applications. For instance, different size hooks can be used to extract molars, premolars and anterior teeth, and different sizes may be implemented for children relative to adults. Similarly, different hooks may be used for extracting teeth in different portions of the mouth.

Figure 3:
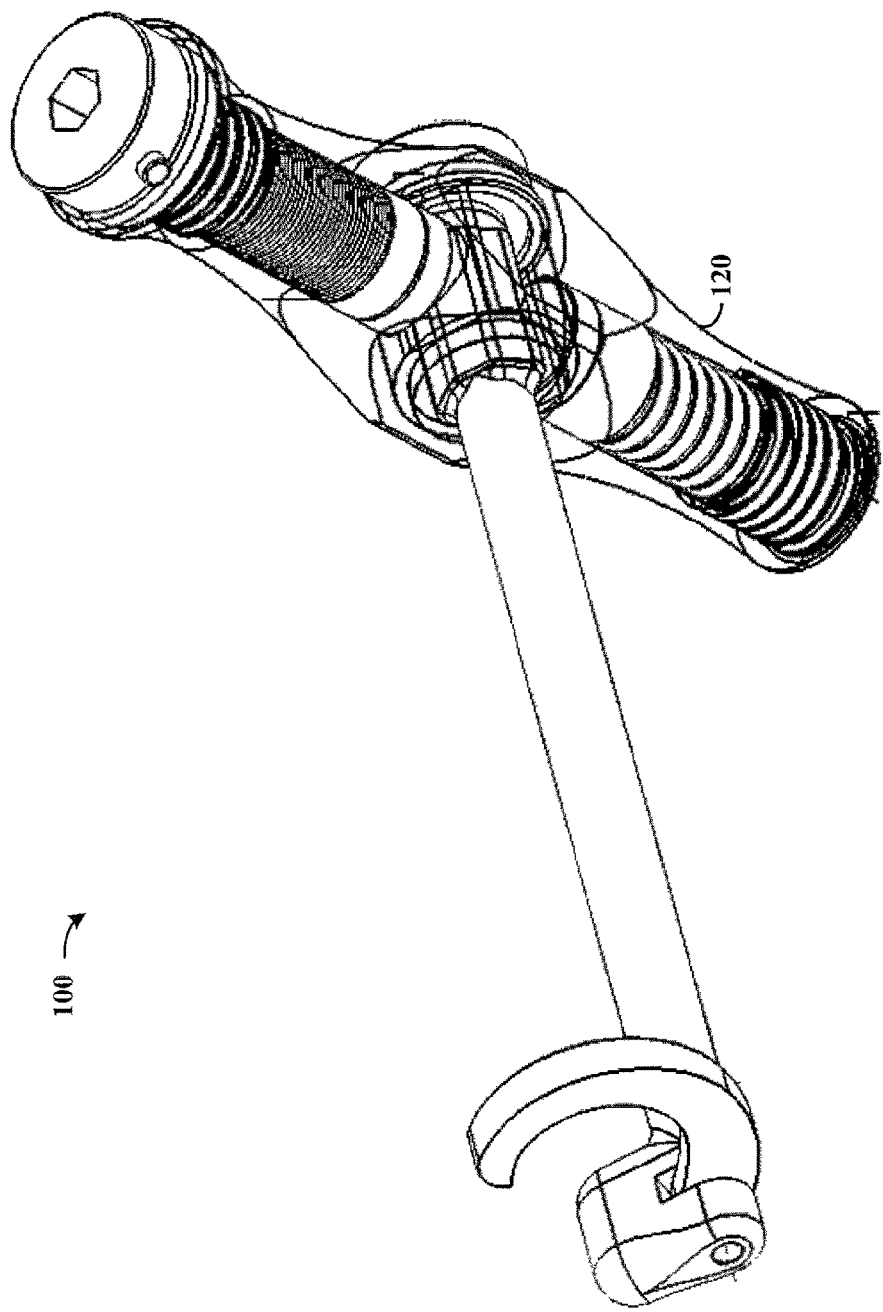
FIG. 3 shows another view of the dental extraction device, in accordance with another example embodiment.

FIG. 3 shows a perspective view, with the nearest portion of the handle 120 corresponding to the right portion of the handle as shown in FIGS. 1 and 2. FIG. 4 shows another vertical view, as viewed from the leftmost end of handle 120, relative to that shown in FIG. 1. FIG. 5 shows a perspective view, with the leftmost portion of the handle 120 shown in FIG. 1 also being on the left in this figure.

Control for torque limiting may be effected in a variety of manners. FIG. 6 shows a torque-limiting dial 600 showing three settings, in accordance with an embodiment. A first range of rotation "1" applies a first level of torque, a second range of rotation "2" provides a second level of torque, and a third range of rotation "3" provides a third level of torque. For instance, the first (low) torque setting may be implemented with anterior teeth, the second (medium) torque setting may be implemented for premolars, and a third (high) torque setting is implemented for molars and canines. In some implementations, component 270 of FIG. 2 is provided with such a torque-limiting dial for setting a torque applied by the apparatus 100. A torque-limiting dial may, for example, be implemented on an end of the handle 120, such as by operating to increase or decrease spring tension at present amounts.

In certain implementations, the first setting is used and, upon reaching the torque limit of the first setting before extracting a tooth, the apparatus is adjusted to the second setting to apply a larger torque. Similarly, adjustment to the third setting can be made if the second setting is insufficient torque—achieved for removing a tooth.

Consistent with the above, the torque-limiting components are implemented in a variety of manners, to suit particular embodiments. In some implementations, a combination of springs and/or torque-bended flat washers is used to provide a range of torque. For instance, some embodiments are directed to providing a 20-40 inch-pound range of torque. Where respective settings are used (e.g., three settings as described above), certain embodiments employ a first setting of 20-25 inch-pounds incisors, 25-35 inch-pounds for premolars, and 35-40 inch-pounds for molars and canines.

Based upon the above discussion and illustrations, those skilled in the art will readily recognize that various modifications and changes may be made to the various embodiments without strictly following the exemplary embodiments and applications illustrated and described herein. For example, various different torque settings may be implemented to suit particular applications. In addition, the various embodiments described herein may be combined in certain embodiments, and various aspects of individual embodiments may be implemented as separate embodiments. Further, certain embodiments may be combined, or aspects of certain embodiments may be implemented separately. Such modifications do not depart from the true spirit and scope of various aspects of the invention, including aspects set forth in the claims.

What is claimed is:

1. A dental extraction apparatus comprising:
an engagement component including a hook configured and arranged to extract a tooth from a patient's mouth by engaging with a side of the tooth via an end portion of the hook and applying a torque to the tooth;
an input torque component, including a handle, configured and arranged to receive an input torque and to translate that input torque to the engagement component; and
a torque controller, including a spring, configured and arranged with the input torque component and the engagement component to limit the torque applied to the tooth at different selectable torque limits, relative to input torque provided via the input torque component, wherein the engagement component includes a coupling configured and arranged to couple to a plurality of different types of hooks, each hook being configured and arranged with a curvature that matches curvature of a particular type of tooth and that facilitates engagement between the hook and tooth for applying the translated torque to the tooth, each hook being configured and arranged with a curvature that matches a curvature of a tooth that is different than tooth curvature that other ones of the hooks match; and
a shaft which is separate from and coupled to the torque controller at a proximal end of the shaft with the engagement component at a distal end of the shaft, the shaft configured and arranged to translate torque from the input torque component to the engagement component, as limited by the torque controller.

2. The apparatus of claim 1, further including a force-absorbing component, including a bumper, adjacent a distal end of the shaft and configured and arranged to cushion the patient's mouth by absorbing force applied via the shaft and providing a pivot point about which the torque is applied to the tooth, and wherein the torque controller is configured and arranged with the input torque component and the engagement component to limit the torque applied to the tooth to a predefined torque, by limiting translation of the input torque to the engagement component based upon an adjustable torque setting provided by the torque controller and corresponding to one of the torque limits.

3. The apparatus of claim 2, wherein the torque controller includes a slip clutch configured and arranged to limit the torque applied to the tooth, based upon the adjustable torque setting.

4. The apparatus of claim 3, wherein the slip clutch is configured and arranged to mechanically slip in response to a torque input that is greater than a current torque-limit setting, and translate the torque input into a torque output that is applied to the tooth and that is limited in value to a torque-limit setting at which the torque controller is set.

5. The apparatus of claim 3, wherein the slip clutch is configured and arranged to translate the input torque to an output torque that is applied to the tooth via the engagement component, and to disengage at least a portion of the input torque from the output torque in response to the input torque exceeding a torque limit.

6. The apparatus of claim 1, wherein the torque controller is configured and arranged to provide different selectable torque settings, each corresponding to a different spring tension, the apparatus further including:
a torque-limiting dial also arranged at the proximal end of the shaft and configured to indicate an amount of torque associated with a torque setting of the torque controller, and
a force-absorbing component, including a bumper, adjacent a distal end of the shaft and configured and arranged to cushion the patient's mouth by absorbing force applied via the shaft and providing a pivot point about which the torque is applied to the tooth.

7. The apparatus of claim 6, wherein the force-absorbing component includes means, adjacent a distal end of the shaft, for providing cushion to the patient's mouth in response to force that is applied via the shaft.

8. The apparatus of claim 1, wherein the torque controller is further configured and arranged to apply a force that sets a torque level at which the input torque component slips relative to the engagement component.

9. The apparatus of claim 1, wherein the handle is configured and arranged for grasping by a human hand, and wherein the torque controller includes a spring configured and arranged to apply pressure against a torque-limiting plate that operates to slip in response to a torsion that provides a radial force against the spring that exceeds a force applied by the spring to the torque-limiting plate.

10. The apparatus of claim 1, wherein the torque controller is configured and arranged to limit the torque applied according to three preset torque limits, including:
a first low torque setting via which the engagement component is configured and arranged for applying sufficient torque to extract anterior teeth;
a second intermediate torque setting via which the engagement component is configured and arranged for applying sufficient torque to extract premolars; and
a third high torque setting via which the engagement component is configured and arranged for applying sufficient torque to extract molars and canines, the engagement component being operable for applying a torque under the second intermediate torque setting that is higher than torque applied under the first low torque setting and lower than torque applied under the third high torque setting.

11. The apparatus of claim 1, wherein the hook is configured and arranged with a curvature that matches curvature of a particular type of tooth and that facilitates engagement between the hook and tooth for applying the translated torque to the tooth.

12. The apparatus of claim 1, wherein the input torque component, including the handle, is configured and arranged for grasping by a human hand.

13. The apparatus of claim 1, wherein the torque controller includes a slip clutch which is configured and arranged to limit the torque applied to the tooth, based upon an adjustable torque setting, and wherein the slip clutch is configured and arranged to mechanically slip in response to a torque input being greater than a current torque-limit setting, and therein to mitigate a tooth fracture while the apparatus is being used to elevate a tooth from an alveolar socket of the patient.

14. A method comprising:
engaging a hook with a side surface of, and applying a torque to, a tooth from a patient's mouth via an engagement component that includes the hook, and aligning the hook with the side surface of the tooth;
translating a received input torque, from an input torque component which includes a handle, along a shaft which is separate from and coupled to a torque controller at a proximal end of the shaft, and to the engagement component which is at a distal end of the shaft; and
limiting the torque applied to the tooth, relative to input torque provided via the input torque component, using the torque controller with the input torque component and the engagement component, wherein the torque controller includes a spring and limiting the torque includes limiting translation of the input torque using a slip clutch, based upon adjustable torque settings provided by the torque controller and corresponding to different torques, by mechanically slipping the slip clutch in response to a torque input that is greater than a current torque-limit setting, and translating the torque input into a torque output that is applied to the tooth and that is limited in value to a torque-limit setting at which the torque controller is set, and wherein engaging with and applying a torque to a tooth includes absorbing a force at a bumper located the engagement component, and therein providing a cushion effect to the patient's mouth by absorbing force applied via the applied torque and providing a pivot point about which the torque is applied to the tooth.

15. The method of claim 14, wherein limiting the torque includes providing via the torque controller:
a first low torque setting via which the engagement component applies sufficient torque to extract anterior teeth;
a second intermediate torque setting via which the engagement component applies sufficient torque to extract premolars; and
a third high torque setting via which the engagement component applies sufficient torque to extract molars and canines, the second intermediate torque setting being higher than the first low torque setting and lower than the third high torque setting.

16. The method of claim 14, wherein the torque controller includes a slip clutch and wherein limiting the torque applied to the tooth further includes using the slip clutch to limit the torque applied to the tooth, based upon the adjustable torque setting, and wherein the slip clutch mechanically slips in response to an event in which a torque input is greater than a current torque-limit setting, and therein mitigate a tooth fracture while elevating a tooth from an alveolar socket of the patient.

17. A method comprising:
engaging a hook with a side surface of, and applying a torque to, a tooth from a patient's mouth via an engagement component that includes the hook, and aligning the hook with the side surface of the tooth, wherein the engagement component includes a coupling configured and arranged to couple to a plurality of different types of hooks, each hook being configured and arranged with a curvature that matches curvature of a particular type of tooth and that facilitates engagement between the hook and tooth for applying a translated torque to the tooth, each hook being configured and arranged with a curvature that matches a curvature of a tooth that is different than tooth curvature that other ones of the hooks match;

translating a received input torque, via an input torque component which includes a handle and via a shaft, to the engagement component; and limiting the torque applied to the tooth, relative to input torque provided via the input torque component, using a torque controller, which is separate from the shaft and arranged at a proximal end of the shaft to provide different selectable torque limits, with the input torque component and the engagement component.

* * * * *